(12) United States Patent
Umbricht et al.

(10) Patent No.: US 7,033,401 B2
(45) Date of Patent: Apr. 25, 2006

(54) 3-AMINOPHENOL DERIVATIVES SUBSTITUTED IN THE 2-POSITION, AND DYES CONTAINING THESE COMPOUNDS

(75) Inventors: Gisela Umbricht, Marly (CH); Franco Jose Rosato, Liebefeld (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 109 days.

(21) Appl. No.: 10/478,732

(22) PCT Filed: Jan. 8, 2003

(86) PCT No.: PCT/EP03/00097

§ 371 (c)(1),
(2), (4) Date: Nov. 24, 2003

(87) PCT Pub. No.: WO03/087034

PCT Pub. Date: Oct. 23, 2003

(65) Prior Publication Data

US 2004/0147515 A1    Jul. 29, 2004

(30) Foreign Application Priority Data

Apr. 18, 2002  (DE) ................ 102 17 270

(51) Int. Cl.
*A61K 7/13* (2006.01)
*C07D 213/06* (2006.01)
(52) U.S. Cl. .......... 8/421; 546/334; 544/335; 549/362; 549/366; 549/440; 549/467; 564/280; 564/307
(58) Field of Classification Search ........ 8/421, 8/405, 406, 408; 546/334; 544/335; 549/362, 549/366, 440, 467; 564/307, 280
See application file for complete search history.

(56) References Cited

U.S. PATENT DOCUMENTS 5,183,941 A  2/1993 Pan et al.
6,001,135 A  12/1999 Rondeau et al.

FOREIGN PATENT DOCUMENTS

DE  40 17 516 A  12/1991
EP  0 850 638 B1  9/1999
WO  95/15144  6/1995
WO  97 30968 A  8/1997
WO  02 02507 A  1/2002

OTHER PUBLICATIONS

"Protective Groups" In Organic Synthesis, Chapter 3, Wiley Interscience 1991, pp. 143-175.
"Protective Groups" In Organic Synthesis, Chapter 7, Wiley Interscience 1991, pp. 494-652.

*Primary Examiner*—Charanjit S. Aulakh
(74) *Attorney, Agent, or Firm*—Michael J. Striker

(57) ABSTRACT

The 3-aminophenol derivatives of formula (I), or the physiologically compatible, water-soluble salts thereof:

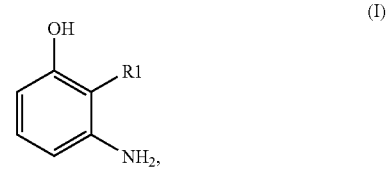

wherein R1 represents a group of formula (II) or a group of formula (III):

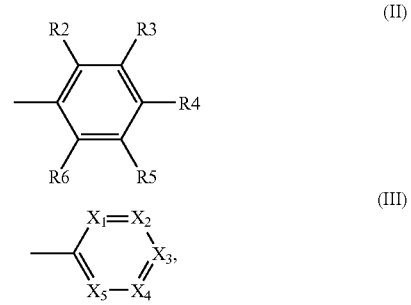

are useful as couplers in hair colorants. Agents for dyeing keratin fibers, especially hair, based on a developer-coupler combination containing these compounds and methods of dyeing using these agents are described.

14 Claims, No Drawings

3-AMINOPHENOL DERIVATIVES SUBSTITUTED IN THE 2-POSITION, AND DYES CONTAINING THESE COMPOUNDS

The present invention relates to novel 3-aminophenol derivatives substituted in the 2-position and to agents for oxidative dyeing of keratin fibers, particularly human hair, containing these agents.

Oxidation dyes have attained substantial importance in the field of keratin fiber dyeing and particularly hair dyeing. The color is generated by reaction of certain developers with certain couplers in the presence of an appropriate oxidant. The developers used for this purpose are, in particular, 2,5-diaminotoluene, 2,5-diaminophenylethyl alcohol, p-aminophenol, 1,4-diaminobenzene and 4,5-diamino-1-(2-hydroxyethyl)pyrazole, whereas suitable couplers are, for example, resorcinol, 2-methylresorcinol, 1-naphthol, 3-aminophenol, 5-amino-2-methylphenol, m-phenylenediamine, 2-amino-4-(2'-hydroxyethyl)aminoanisole, 1,3-diamino-4-(2'-hydroxyethoxy)-benzene and 2,4-diamino-5-fluorotoluene.

In addition to being able to produce colors of the desired intensity, oxidation dyes used for dyeing human hair must meet many other requirements. For example, such dyes must be unobjectionable from a toxicological and dermatological standpoint, and the hair colorations obtained must be highly resistant to light, permanent waving, acids and rubbing. In any case, however, in the absence of exposure to light, rubbing and chemical agents such colorations must remain stable for a period of at least 4 to 6 weeks. Moreover, it must be possible, by a combination of suitable developers and couplers, to produce a wide range of different color shades.

Although many couplers are already known, with the currently known colorants it is not possible to meet the requirements placed on a colorant in every respect. Hence, a need continues to exist for novel couplers that will meet the aforesaid requirements to an especially high degree.

We have now found that certain 3-aminophenol derivatives of general formula (I) meet the requirements placed on couplers to an especially high degree and with known developers give intense and unusually light-fast and wash-fast color shades.

Hence, the object of the present invention are novel 3-aminophenol derivatives of the following formula (I) or physiologically compatible, water-soluble salts thereof,

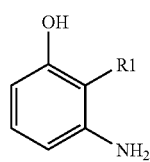
(I)

wherein R1 stands for a group of formula (II) or (III)

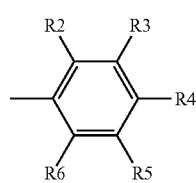
(II)

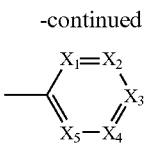
(III)

wherein

R2, R3, R4, R5 and R6 independently of each other denote hydrogen, a halogen atom (F, Cl, Br, I), a cyano group, a hydroxyl group, a $C_1$–$C_4$-alkoxy group, a phenoxy group, a $C_2$–$C_4$-hydroxyalkoxy group, a $C_1$–$C_8$-alkyl group, a phenyl group, a $C_1$–$C_4$-alkyl thioether group, a mercapto group, a nitro group, an amino group, a $C_1$–$C_4$-alkylamino group, a hydroxy-($C_2$–$C_4$)-alkylamino group, a di($C_1$–$C_4$)-alkylamino group, a di-[hydroxy($C_2$–$C_4$)-alkyl]amino group, a [dihydroxy-($C_3$–$C_4$)-alkyl]amino group, a [hydroxy-($C_2$–$C_4$)-alkyl]-$C_1$–$C_4$-alkylamino group, a trifluoromethyl group, a formyl group, an acetyl group, a trifluoroacetyl group, a trimethylsilyl group, a ($C_1$–$C_4$)-hydroxyalkyl group, a ($C_2$–$C_4$)-dihydroxyalkyl group, a ($C_1$–$C_4$)-aminoalkyl group or a ($C_1$–$C_4$)-cyanoalkyl group, or two adjacent R2 to R6 groups together with the remainder of the molecule form a heterocyclic or carbocyclic, substituted or unsubstituted ring;

$X_1$, $X_2$, $X_3$, $X_4$ and $X_5$ independently of each other denote nitrogen or a C—R7 group, C—R8 group, C—R9 group, C—R10 group or C—R11 group, provided that at least one and at the most three of the $X_1$ to $X_5$ groups denote nitrogen; and R7, R8, R9, R10 and R11 independently of each other denote hydrogen, a halogen atom (F, Cl, Br, I), a cyano group, a $C_1$–$C_6$-alkyl group, a ($C_1$–$C_4$)-alkyl thioether group, a mercapto group, a nitro group, an amino group, a $C_1$–$C_4$-alkylamino group, a hydroxy-($C_2$–$C_4$)-alkylamino group, a di($C_1$–$C_4$)-alkylamino group, a di[hydroxy($C_2$–$C_4$)-alkyl] amino group, a [dihydroxy-($C_3$–$C_4$)-alkyl]amino group, a [hydroxy-($C_2$–$C_4$)-alkyl]-$C_1$–$C_4$-alkylamino group, a trifluoromethyl group, a formyl group, an acetyl group, a trifluoroacetyl group, a trimethylsilyl group, a carbamoyl group, a ($C_1$–$C_4$)-hydroxyalkyl group or a ($C_2$–$C_4$)-dihydroxyalkyl group.

Suitable compounds of formula (I) are, for example:
6-amino-[1,1'-biphenyl]-2-ol, 6-amino-4'-methyl-[1,1'-biphenyl]-2-ol, 6-amino-3'-methyl-[1,1'-biphenyl]-2-ol, 6-amino-2'-methyl-[1,1'-biphenyl]-2-ol, 6-amino-2',3'-dimethyl-[1,1'-biphenyl]-2-ol, 6-amino-2',4'-dimethyl-[1,1'-biphenyl]-2-ol, 6-amino-2',5'-dimethyl-[1,1'-biphenyl]-2-ol, 6-amino-2',6'-dimethyl-[1,1'-biphenyl]-2-ol, 6-amino-3',4'-dimethyl-[1,1'-biphenyl]-2-ol, 6-amino-3',5'-dimethyl-[1,1'-biphenyl]-2-ol, 6-amino-3',6'-dimethyl-[1,1'-biphenyl]-2-ol, 6-amino-2',4',5'-trimethyl-[1,1'-biphenyl]-2-ol, 6-amino-2',4',6'-trimethyl-[1,1'-biphenyl]-2-ol, 6-amino-2',3',4'-trimethyl-[1,1'-biphenyl]-2-ol, 6-amino-2',3', 5'-trimethyl-[1,1'-biphenyl]-2-ol, 6-amino-2',3',6'-trimethyl-[1,1'-biphenyl]-2-ol, 6-amino-4'-chloro-[1,1'-biphenyl]-2-ol, 6-amino-3'-chloro-[1,1'-biphenyl]-2-ol, 6-amino-2'-chloro-[1,1'-biphenyl]-2-ol, 6-amino-4'-fluoro-[1,1'-biphenyl]-2-ol, 6-amino-3'-fluoro-[1,1'-biphenyl]-2-ol, 6-amino-2'-fluoro-[1,1'-biphenyl]-2-ol, 6-amino-4'-bromo-[1,1'-biphenyl]-2-ol, 6-amino-3'-bromo-[1,1'-biphenyl]-2-ol, 6-amino-2'-bromo-[1,1'-biphenyl]-2-ol, 6-amino-3',5'-dichloro-[1,1'- biphenyl]-2-ol, 6-amino-3',5'-difluoro-[1,1'-biphenyl]-2-ol, 6-amino-3'-bromo-5'-methyl-[1,1'-biphenyl]-2-ol, 6-amino-4'-(trifluoromethyl)-[1,1'-biphenyl]-2-ol, 6-amino-3'-(trifluoromethyl)-[1,1'-biphenyl]-2-ol, 6-amino-2'-(trifluoromethyl)-[1,1'-biphenyl]-2-ol, 6-amino-4'-nitro-[1,1'-biphenyl]-2-ol, 6-amino-3'-nitro-[1,1'-biphenyl]-2-ol, 6-amino-2'-nitro-[1,1'-biphenyl]-2-ol, 6-amino-5'-methyl-3'-nitro-[1,1'-biphenyl]-2-ol, 6-amino-4'-methyl-3'-nitro-[1,1'-biphenyl]-2-ol, 6-amino-2'-methyl-3'-nitro-[1,1'-biphenyl]-2-ol, 6-amino-2'-nitro-4'-(trifluoromethyl)-[1,1'-biphenyl]-2-ol, 6-amino-3'-nitro-5'-(trifluoromethyl)-[1,1'-biphenyl]-2-ol, 6-amino-3'-nitro-4'-(trifluoromethyl)-[1,1'-biphenyl]-2-ol, 6-amino-3'-nitro-2'-(trifluoromethyl)-[1,1'-biphenyl]-2-ol, 6'-amino-2'-hydroxy-[1,1'-biphenyl]-4-carbonitrile, 6'-amino-2'-hydroxy-[1,1'-biphenyl]-3-carbonitrile, 6-amino-4'-methoxy-[1,1'-biphenyl]-2-ol, 6-amino-3'-methoxy-[1,1'-biphenyl]-2-ol, 6-amino-2'-methoxy-[1,1'-biphenyl]-2-ol, 6-amino-4'-ethoxy-[1,1'-biphenyl]-2-ol, 6-amino-3'-ethoxy-[1,1'-biphenyl]-2-ol, 6-amino-2'-ethoxy-[1,1'-biphenyl]-2-ol, 6-amino-3',4'-dimethoxy-[1,1'-biphenyl]-2-ol, 6-amino-3',5'-dimethoxy-[1,1'-biphenyl]-2-ol, 6-amino-2',3'-dimethoxy-[1,1'-biphenyl]-2-ol, 6-amino-2',4'-dimethoxy-[1,1'-biphenyl]-2-ol, 6-amino-2',5'-dimethoxy-[1,1'-biphenyl]-2-ol, 3-amino-2-(1,3-benzodioxol-5-yl)phenol, 6-amino-4'-methoxy-3'-methyl-[1,1'-biphenyl]-2-ol, 6-amino-4'-methoxy-2'-nitro-[1,1'-biphenyl]-2-ol, 6-amino-4'-methoxy-3'-nitro-[1,1'-biphenyl]-2-ol, 6-amino-4'-phenoxy-[1,1'-biphenyl]-2-ol, 6-amino-4'-methylthio-[1,1'-biphenyl]-2-ol, 6-amino-3'-methylthio-[1,1'-biphenyl]-2-ol, 6-amino-2'-methylthio-[1,1'-biphenyl]-2-ol, 6-amino-[1,1'-biphenyl]-2,4'-diol, 6-amino-[1,1'-biphenyl]-2,3'-diol, 6-amino-[1,1'-biphenyl]-2,2'-diol, 2,2',3'-trihydroxy-6-amino-[1,1'-biphenyl], 2,2'4'-trihydroxy-6-amino-[1,1'-biphenyl], 2,2'5'-trihydroxy-6-amino-[1,1'-biphenyl], 2,2'6'-trihydroxy-6-amino-[1,1'-biphenyl], 2,3',4'-trihydroxy-6-amino-[1,1'-biphenyl], 2,3',5'-trihydroxy-6-amino-[1,1'-biphenyl], 6-amino-2'-methyl-[1,1'-biphenyl]-2,4'-diol, 2',6-diamino-[1,1'-biphenyl]-2-ol, 3',6-diamino-[1,1'-biphenyl]-2-ol, 4',6-diamino-[1,1'-biphenyl]-2-ol, 4',6-diamino-[1,1'-biphenyl]-2,2'-diol, 3',6-diamino-[1,1'-biphenyl]-2,2'-diol, 3',6-diamino-[1,1'-biphenyl]-2,4'-diol, 3',6-diamino-[1,1'-biphenyl]-2,5'-diol, 3',6-diamino-[1,1'-biphenyl]-2,6'-diol, 2',3',6-triamino-[1,1'-biphenyl]-2-ol, 2',4',6-triamino-[1,1'-biphenyl]-2-ol, 2',5',6-triamino-[1,1'-biphenyl]-2-ol, 2',6,6'-triamino-[1,1'-biphenyl]-2-ol, 3',4',6-triamino-[1,1'-biphenyl]-2-ol, 3',5',6-triamino-[1,1'-biphenyl]-2-ol, 1-(6'-amino-2'-hydroxy-[1,1'-biphenyl]-4-yl)-ethanone, 6-amino-1,1',3',1"-terphenyl-2-ol, 6-amino-1,1',4',1"'-terphenyl-2-ol, 6-amino-4'-(aminomethyl)-[1,1'-biphenyl]-2-ol, 6-amino-3'-(aminomethyl)-1,1'-biphenyl-2-ol, 6-amino-2'-(aminomethyl)-[1,1'-biphenyl]-2-ol, (6'-amino-2'-hydroxy-[1,1'-biphenyl]-4-yl)acetonitrile, (6'-amino-2'-hydroxy-[1,1'-biphenyl]-3-yl)acetonitrile, (6'-amino-2'-hydroxy-[1,1'-biphenyl]-2-yl)acetonitrile, 6'-amino-2'-hydroxy-[1,1'-biphenyl]-2-carbaldehyde, 6'-amino-2'-hydroxy-1,1'-biphenyl-3-carbaldehyde, 6'-amino-2'-hydroxy-[1,1'-biphenyl]-4-carbaldehyde, 3-amino-2-(1-naphthyl)phenol, 3-amino-2-(2-naphthyl)phenol, 3-amino-2-(2,3-dihydrobenzo[1,4]-dioxin-6-yl)phenol, 3-amino-2-(2,3-dihydrobenzo[1,4]dioxin-5-yl)phenol, 3-amino-2-(2,3-dihydrobenzofuran-5-yl)phenol, 3-amino-2-(2,3-dihydrobenzofuran-4-yl)phenol, 3-amino-2-(4-pyridinyl)phenol, 3-amino-2-(3-pyridinyl)phenol, 3-amino-2-(2-pyridinyl)phenol, 3-amino-2-(3-methyl-2-pyridinyl)phenol, 3-amino-2-(4-methyl-2-pyridinyl)phenol, 3-amino-2-(5-methyl-2-pyridinyl)phenol, 3-amino-2-(6-methyl-2-pyridinyl)phenol, 3-amino-2-(3-chloro-2-pyridinyl)phenol, 3-amino-2-(4-chloro-2-pyridinyl)phenol, 3-amino-2-(5-chloro-2-pyridinyl)phenol, 3-amino-2-(6-chloro-2-pyridinyl)phenol, 3-amino-2-(3-fluoro-2-pyridinyl)phenol, 3-amino-2-(4-fluoro-2-pyridinyl)phenol, 3-amino-2-(5-fluoro-2-pyridinyl)phenol, 3-amino-2-(6-fluoro-2-pyridinyl)phenol, 3-amino-2-(3-trifluoromethyl-2-pyridinyl)phenol, 3-amino-2-(4-trifluoromethyl-2-pyridinyl)phenol, 3-(amino-2-(5-trifluoromethyl-2-pyridinyl)phenol, 3-(amino-2-(6-trifluoromethyl-2-pyridinyl)phenol, 3-amino-2-(3-nitro-2-pyridinyl)phenol, 3-amino-2-(4-nitro-2-pyridinyl)phenol, 3-amino-2-(5-nitro-2-pyridinyl)phenol, 3-amino-2-(6-nitro-2-pyridinyl)phenol, 3-amino-2-(2-methyl-3-pyridinyl)phenol, 3-amino-2-(4-methyl-3-pyridinyl)phenol, 3-amino-2-(5-methyl-3-pyridinyl)phenol, 3-amino-2-(6-methyl-3-pyridinyl)phenol, 3-amino-2-(2-chloro-3-pyridinyl)phenol, 3-amino-2-(4-chloro-3-pyridinyl)phenol, 3-amino-2-(5-chloro-3-pyridinyl)phenol, 3-amino-2-(6-chloro-3-pyridinyl)phenol, 3-amino-2-(2-bromo-3-pyridinyl)phenol, 3-amino-2-(4-bromo-3-pyridinyl)phenol, 3-amino-2-(5-bromo-3-pyridinyl)phenol, 3-amino-2-(6-bromo-3-pyridinyl)phenol, 3-amino-2-(2-nitro-3-pyridinyl)phenol, 3-amino-2-(4-nitro-3-pyridinyl)phenol, 3-amino-2-(5-nitro-3-pyridinyl)phenol, 3-amino-2-(6-nitro-3-pyridinyl)phenol, 3-amino-2-(5-pyrimidinyl)-phenol and 3-amino-2-(4-pyrimidinyl)phenol as well as the physiologically compatible, water-soluble salts thereof.

Preferred are compounds of formula (I) wherein:
(i) R1 denotes a group of formula (II) with R2 or R6 denoting hydrogen, or
(ii) R1 denotes a group of formula (III) with $X_1$ and $X_6$ denoting C—R7 or C—R11, and R7 or R11 denoting hydrogen.

Particularly preferred are the following compounds of formula (I); 6-amino-3'-methoxy-[1,1'-biphenyl]-2-ol, 6-amino-[1,1'-biphenyl]-2,4'-diol, 3-amino-2-(2,3-dihydrobenzo[1,4]dioxin-6-yl)phenol, 3-amino-2-(2,3-dihydrobenzofuran-5-yl)phenol, 3-amino-2-(3-pyridinyl)phenol, 3-amino-2-(4-pyridinyl)phenol and 3-amino-2-(5-pyrimidinyl)phenol and their physiologically compatible, water-soluble salts.

The compounds of formula (I) can be used as the free bases as well as in the form of their physiologically compatible salts of inorganic or organic acids, for example hydrochloric acid, sulfuric acid, phosphoric acid, acetic acid, propionic acid, lactic acid or citric acid.

The aminophenol derivatives of formula (I) of the invention can be prepared by methods of synthesis known from the literature, for example a) by tetrakis(triphenylphosphine)palladium(0)-catalyzed coupling of a halogen-substituted 3-aminophenol derivative of formula (IV)

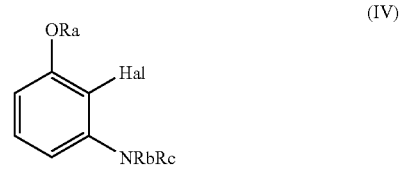

with a boric acid derivative of formula (IIa) or (IIIa)

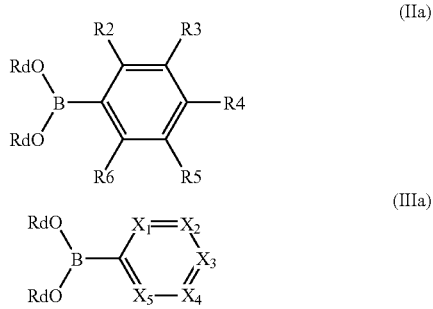

followed by removal of the protective group needed for the coupling reaction and by reduction of an optionally present nitro group; or b) tetrakis(triphenylphosphine)palladium(0)-catalyzed coupling of an appropriate substituted 3-aminophenolboric acid derivative of formula (V)

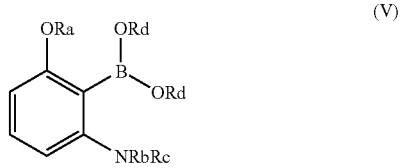

with a halogen-substituted compound of formula (IIb) or (IIIb)

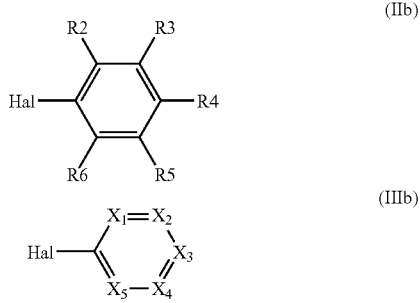

followed by removal of the protective group needed for the coupling reaction and by reduction of an optionally present nitro group, the other groups used in formulas (IIa), (IIb), (IIIa), (IIIb), (IV) and (V) having the following meaning:

Ra denotes a protective group as described, for example, in the chapter on "Protective Groups" in Organic Synthesis, chapter 3, Wiley Interscience, 1991;

Rb and Rc independently of each other denote hydrogen or a protective group as described, for example, in the chapter on "Protective Groups" in Organic Synthesis, chapter 7, Wiley Interscience, 1991, or Rb and Rc together with the N-atom form a nitro group;

Rd denotes hydrogen or the two Rd groups together with the —O—B—O— group form an unsubstituted or substituted five-membered or six-membered cycloaliphatic ring;

Hal denotes F, Cl, Br or I; and

R2, R3, R4, R5 and R6 and $X_1$, $X_2$, $X_3$, $X_4$ and $X_5$ have the same meaning as in formulas (II) or (III).

The 3-aminophenol derivatives of formula (I) are readily water-soluble and give colorations of excellent color intensity and color stability, particularly in terms of light fastness, wash fastness and rubbing fastness. Moreover, they have excellent storage stability particularly as constituents of the oxidative colorants described in the following.

Another object of the present invention is therefore an agent for coloring keratin fibers, for example wool, furs, feathers or hair and particularly human hair, said agent being based on a developer-coupler combination and being characterized in that it contains at least one 3-aminophenol derivative of formula (I) or a physiologically compatible, water-soluble salt thereof.

The 3-aminophenol derivatives of formula (I) are present in the colorant of the invention in a total amount from about 0.005 to 20 weight percent, an amount from about 0.01 to 5 wt. % and particularly from 0.1 to 2.5 wt. % being preferred.

Preferred developers are 1,4-diaminobenzene (p-phenylenediamine), 1,4-diamino-2-methylbenzene (p-toluylenediamine), 1,4-diamino-2,6-dimethylbenzene, 1,4-diamino- 3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)-benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(1-hydroxyethyl)benzene, 1,4-diamino-2-(2-hydroxyethyl)benzene, 1,4-diamino-2-(1-methylethyl)benzene, 1,3-bis-[(4-aminophenyl)(2-hydroxyethyl)amino]-propanol, 1,4-bis-[(4-aminophenyl)amino]butane, 1,8-bis-(2,5-diaminophenoxy)-3,6-dioxaoctane, 4-aminophenol, 4-amino-3-methylphenol,4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

Moreover, besides the compounds of formula (I) the colorant of the invention can also contain other known couplers, for example N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 1,3-diamino-4-(2,3-dihydroxypropoxy)- benzene, 1,3-diamino-4-(3-hydroxypropoxy)-benzene, 1,3-diamino-4-(2-methoxyethoxy)-benzene, 2,4-diamino-1,5-di(2-hydroxyethoxy)-benzene, 1-(2-aminoethoxy)-2,4-diamino benzene, 2-amino-1-(2-hydroxyethoxy)-4-methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl) aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)-amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

The couplers and developers can be contained in the colorant of the invention either individually or in admixture with each other, the total amount of couplers and developers in the colorant of the invention (based on the total amount of colorant) being from about 0.005 to 20 weight percent, preferably from about 0.01 to 5 weight percent and particularly from 0.1 to 2.5 weight percent, each.

The total amount of the developer-coupler combination contained in the colorant described herein is preferably from about 0.01 to 20 weight percent, an amount from about 0.02 to 10 weight percent and particularly from 0.2 to 6 weight percent being especially preferred. In general, the developers and couplers are used in equimolar amounts. However, it is not disadvantageous if the developers are present in a certain excess or deficiency with respect to such an amount.

Moreover, the colorant of the invention can also contain additional dye components, for example 6-amino-2-methylphenol and 2-amino-5-methylphenol as well as common synthetic or natural direct dyes, for example vegetable dyes or synthetic direct dyes from the group of acid or basic dyes (for example the cationic dyes described in WO 95/15144 or European Unexamined Patent Application EP 0 850 638), triphenylmethane dyes, aromatic nitro dyes, azo dyes and disperse dyes. The colorants of the invention can contain these dye components in an amount from about 0.1 to 4 weight percent.

Naturally, the additional couplers and the developers and other dye components, provided they are bases, can also be used in the form of their physiologically compatible salts of organic or inorganic acids, for example hydrochloric acid or sulfuric acid, or—if they contain aromatic OH— groups—in the form of salts of bases, for example as alkali phenoxides.

Moreover, if the colorants are used for dyeing hair, they can also contain common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be formulated, for example, as a solution, particularly an aqueous or aqueous-alcoholic solution. A particularly preferred formulation, however, is a cream, gel or emulsion. Such a preparation consists of a mixture of dye components and additives commonly used for such preparations.

Common additives to solutions, creams, emulsions or gels are, for example, solvents such as water, lower aliphatic alcohols, for example ethanol, propanol or isopropanol, glycerol or glycols such as 1,2-propylene glycol; moreover wetting agents or emulsifiers from the classes of anionic, cationic, amphoteric or nonionic surface-active substances such as, for example, the fatty alcohol sulfates, ethoxylated fatty alcohol sulfates, alkylsulfonates, alkylbenzene-sulfonates, alkyltrimethylammonium salts, alkylbetaines, ethoxylated fatty alcohols, ethoxylated nonylphenols, fatty alkanolamides and ethoxylated fatty esters, furthermore thickeners such as the higher fatty alcohols, starch, cellulose derivatives, petrolatum, paraffin oil and fatty acids; moreover hair-care agents such as cationic resins, lanolin derivatives, cholesterol, pantothenic acid and betaine. The said constituents are used in amounts commonly employed for such purposes, for example the wetting agents and emulsifiers at a concentration from about 0.5 to 30 weight percent, the thickeners in an amount from about 0.1 to 30 weight percent and the hair-care agents at a concentration from about 0.1 to 5 weight percent.

Depending on the composition, the colorant of the invention can be weakly acidic, neutral or alkaline. In particular, it has a pH from 6.5 to 11.5, the adjustment to a basic value preferably being achieved with ammonia. However, amino acids and/or organic amines, for example monoethanolamine ortriethanolamine, or inorganic bases, for example sodium hydroxide or potassium hydroxide can also be used. For pH adjustment in the acidic range, an inorganic or organic acid, for example phosphoric acid, acetic acid, citric acid or tartaric acid, can be used.

For use in oxidative dyeing of hair, the afore-described colorant is mixed with an oxidant just before use and the resulting mixture is applied to the hair in an amount sufficient for the hair treatment, in general in an amount from about 60 to 200 grams, depending on the fullness of the hair.

Suitable oxidants for developing the hair coloration are mainly hydrogen peroxide or the compounds of addition thereof to urea, melamine, sodium borate or sodium carbonate in the form of a 3 to 12%, preferably 6% aqueous solution. Atmospheric oxygen can also be used. If a 6% hydrogen peroxide solution is used as oxidant, the weight ratio of hair colorant to oxidant is from 5:1 to 1:2 and preferably 1:1. Larger amounts of oxidant are used primarily at higher dye concentrations in the hair colorant or when more pronounced hair bleaching is wanted at the same time. The mixture is allowed to act on the hair at 15 to 50° C. for about 10 to 45 minutes, preferably for 30 minutes, after which the hair is rinsed with water and dried. Optionally, following this rinsing the hair is washed with a shampoo and optionally post-rinsed with a weak organic acid, for example citric acid or tartaric acid. The hair is then dried.

The colorant of the invention containing a 3-aminophenol derivative of formula (I) as coupler gives colorations of excellent color stability, particularly in terms of light fastness, wash fastness and rubbing fastness. As far as the coloring properties are concerned, depending on the kind and composition of the dye components, the colorant of the invention provides a wide range of different color shades ranging from blond to brown, purple, violet, blue and black. Said shades are characterized by high color intensity. Furthermore, the very good coloring properties of the colorant of the present patent application are, in particular, characterized by the fact that this colorant also makes it possible to dye gray, chemically not previously damaged hair with good covering power and without any problems.

The following examples are intended to illustrate the subject matter of the invention more closely without limiting its scope.

EXAMPLES

Examples 1 to 17

Synthesis of 3-Aminophenol Derivatives of General Formula (I)

A. Synthesis of 2-bromo-3-nitrophenol

A solution of 10.5 g (152 mmol) of sodium nitrite in 40 mL of water was added slowly and dropwise to a suspension of 23.1 g (150 mmol) of 2-amino-3-nitrophenol in 40 ml of a 48% hydrobromic acid solution and 12 mL of water at 0° C. The mixture was then allowed to agitate at 0° C. for 15 minutes. Subsequently, a suspension of 22.5 g of copper(I) bromide ($Cu_2Br_2$; 78.7 mmol) in 75 mL of a 48% hydrobromic acid solution was added dropwise, and the mixture was allowed to agitate at 0° C. for 15 minutes and then at 100° C. for 1 hour. The reaction mixture was then cooled to about 5° C. and filtered, and the filter cake was washed with a small amount of water. This filter cake was then taken up with ethyl acetate and filtered through silica gel. The solvent was then evaporated to dryness under vacuum.

This gave 32.2 g. (98% of the theoretical) of 2-bromo-3-nitrophenol. The crude product thus obtained was used in the next step without additional purification.

$^1$H-NMR (300 MHz, $CDCl_3$): δ=7.47 ppm (dd, J=1.5 Hz/7.8 Hz, 1H, CH); 7.37 ppm (t, 1H, J=8.1 Hz, CH); 7.26 ppm (dd, J=1.5 Hz/8.1 Hz, 1H, CH); 6.08 ppm (s, 1H, OH). EI-MS: 219/217 [$M^+$] (40); 161/159 [$M^+$—C—$NO_2$] (24)

B. Synthesis of 2-bromo-1-(methoxymethoxy)-3-nitrobenzene 15 g (69 mmol) of 2-bromo-3-nitrophenol from step A was dissolved in 150 mL of dry acetonitrile and to it was added portionwise at 0° C. 3.5 g (117 mmol) of an 80% sodium hydride suspension. A solution of 6.1 g (75 mmol) of chloromethoxymethane in 50 mL of dry acetonitrile was then added. At the end of the addition, the mixture was allowed to agitate overnight at room temperature. Ten mL of ethanol was added to decompose excess sodium hydride. The reaction mixture was then filtered, and the filtrate was evaporated to dryness in a rotary evaporator under vacuum.

This gave 14.6 g (81% of the theoretical) of 2-bromo-1-(methoxymethoxy)-3-nitrobenzene as a brown oil.

The crude product thus obtained was used in the next step without further purification.

$^1$H-NMR (300 MHz, DMSO): δ=7.60–7.48 ppm (m, 3H, arom. —CH); 5.41 ppm (s, 2H, $CH_2$); 3.44 ppm (s, 3H, $CH_3$). MS (API-ES neg.): 218/216 [M–H]$^-$ (100).

C. Synthesis of 3-aminophenols of Formula (I)

0.26 g (1 mmol) of 2-bromo-1-(methoxymethoxy)-3-nitrobenzenefrom step B and 1.5 mmol of the corresponding boric acid derivative were dissolved in 5 mL of 1,2-dimethoxyethane under argon. Then, 0.18 g (0.15 mmol) of tetrakis(triphenylphosphine)palladium(0) complex and 0.8 mL of a 2N aqueous potassium carbonate solution were added, and the reaction mixture was heated to 100° C. At the end of the reaction, the reaction mixture was poured into 10 mL of ethyl acetate, the organic phase was extracted with 5 mL of water and the aqueous phase was back-extracted twice with ethyl acetate. The combined organic phases were then dried with magnesium sulfate, and the solvent was distilled off in a rotary evaporator. The residue was purified on silica gel using heptane/ethyl acetate.

The product thus obtained was dissolved in 5 mL of ethanol and hydrogenated with gaseous hydrogen in the presence of about 50 mg of palladium (10% on active charcoal) at room temperature and normal pressure. At the end of the reaction, the reaction product was filtered through Cellite® and then concentrated. The resulting residue was treated with 1 mL of a 2.9-molar ethanolic hydrochloric acid solution or with 4-molar hydrochloric acid solution in dioxane. The reaction mixture was allowed to agitate for about one hour at room temperature. At the end of the reaction, the precipitate was filtered off, washed with ethanol (or dioxane) and then dried. If no precipitation has occurred, the solvent can be evaporated in a rotary evaporator.

1. 6-Amino-1,1'-biphenyl-2-ol Hydrochloride

Boric acid derivative used: phenylboric acid

Yield: 0.088 g (44% of the theoretical) $^1$H-NMR (300 MHz, DMSO): δ=9.80 ppm (s, 1H, OH); 7.48–7.35 ppm (m, 5H, arom. H); 7.22 ppm (t, J=7.5 Hz, 1H, arom. H); 6.89 ppm (t, J=7.5 Hz, 2H, arom. H); 4.1–3.3 ppm (br, 3H, $NH_3^+$). MS (API-ES pos.): 186 [M+H]$^+$ (100).

Boric acid derivative used: 3-aminophenylboric acid

Yield; 0.154 g (34% of the theoretical) MS (API-ES pos.): 201 [M+H]$^+$ (60); 223 [M+Na]$^+$ (60).

3. 6-Amino-3'-methoxy-1,1'-biphenyl-2-ol hydrochloride

Boric acid derivative used: 3-methoxyphenylboric acid

Yield: 0.141 g (58% of the theoretical) $^1$H-NMR (300 MHz, DMSO): δ=9.80 ppm (s, 1H. OH); 7.38 ppm (t, J=8.1 Hz, 1H, arom. H); 7.22 ppm (t, J=8.1 Hz, 1H, arom. H): 6.99–6.87 ppm (m, 5H, arom. H); 3.80 ppm (s, 3H, $CH_3$); 4.1–3.3 ppm (br, 3H, $NH_3^+$) MS (API-ES pos.): 216 [M+H]$^+$ (100); 238 [M+Na]$^+$ (25).

4. 6-Amino-4'-methoxy-1,1'-bihenyl-2-ol hydrochloride

Boric acid derivative used: 4-methoxyphenylboric acid

Yield: 0.055 g (21% of the theoretical) $^1$H-NMR (300 MHz, DMSO): δ=9.70 ppm (s, 1H, OH); 7.27 ppm (d, J=8.6 Hz, 2H, arom. H); 7.18 ppm (t, J=8.1 Hz, 1H, arom. H); 7.02 ppm (d, J=8.6 Hz, 2H, arom. H.); 6.84 ppm (t, J=8.1 Hz, 2H, arom. H); 3.82 ppm (s, 3H, $CH_3$); 3.7–3.3 ppm (br, $NH_3^+$). MS (API-ES pos.): 216 [M+H]$^+$ (100).

5. 3-Amino-2-(1,3-benzodioxol-5-yl)phenol hydrochloride

Boric acid derivative used: 3,4-methylenedioxyphenylboric acid

Yield: 0.153 g (59% of the theoretical) $^1$H-NMR (300 MHz, DMSO): δ=9.81 ppm (s, 1H, OH); 7.20 ppm (t, J=8.1 Hz, 1H, arom. H); 7.01 ppm (d, J=7.9 Hz, 1H, arom. H); 6.92–6.79 ppm (m. 4H, arom. H); 6.80 ppm (s, 2H $CH_2$); 3.8–3.2 ppm (br, $NH_3^+$). MS (API-ES pos.): 230 [M+H]$^+$ (75). H); 6.80 ppm (s, 2H $CH_2$); 3.8–3.2 ppm (br, $NH_3^+$). MS (API-ES pos.): 230 [M+H]$^+$ (75).

6. 6-Amino-2',4'-dimethoxy-1,1'-biphenyl-2-ol hydrochloride

Boric acid derivative used: 2,4-dimethoxyphenylboric acid

Yield: 0.078 g (29% of the theoretical) MS (API-ES pos.): 246 [M+H]$^+$ (100).

7. 6-Amino-4'-methyl-1,1'-biphenyl-2-ol hydrochloride

Boric acid derivative used: 4-tolylboric acid

Yield: 0.177 g (78% of the theoretical) $^1$H-NMR (300 MHz, DMSO): δ=9.76 ppm (s, 1H, OH); 7.29–7.18 ppm (m, 5H, arom. H); 6.88 ppm (t, J=8.7 Hz, 2H, arom. H); 3.8–3.2 ppm (br, NH$_3^+$); 2.38 ppm (s, 3H, CH$_3$). MS (API-ES pos.): 200 [M+H]$^+$ (100).

8. 3-Amino-2-(1-naphthyl)phenol hydrochloride

Boric acid derivative used: 1-naphthylboric acid

Yield: 0.140 g (51% of the theoretical) $^1$H-NMR (300 MHz, DMSO): δ=9.66 ppm (s, 1H, OH); 8.01 ppm (d, J=8.1 Hz, 2H, arom. H); 7.65–7.13 ppm (m, 6H, arom. H); 6.90 ppm (d, J=8.1 Hz, 1H, arom. H); 3.8–3.2 ppm (br, NH$_3^+$). MS (API-ES pos.): 236 [M+H]$^+$ (100).

Yield: 0.104 g (41% of the theoretical) MS (API-ES pos.): 214 [M+H]$^+$ (100).

10. 3-Amino-2-(2,3-dihydrobenzo[1,4]dioxin-6-yl)phenol hydrochloride

Boric acid derivative used: 2,3-dihydro-1,4-benzodioxin-6-ylboric acid

Yield: 0.05 g (23% of the theoretical) MS (API-ES nos.): 244 [M+H]$^+$ (100).

11. 3-Amino-2-(2,3-dihydrobenzofuran-5-yl)phenol hydrochloride

Boric acid derivative used: 2,3-dihydro-1-benzofuran-5-ylboric acid

Yield: 0.07 g (26% of the theoretical) $^1$H-NMR (300 MHz, DMSO): δ=9.62 ppm (s, 1H, OH); 7.17–7.13 ppm (m, 2H, arom, H); 7.02 ppm (d, J=7.4 Hz, 1H, arom. H); 6.86–6.77 ppm (m, 3H, arom. H); 4.59 ppm (t, J=8.6 Hz, 2H, CH$_2$); 3.22 ppm (t, J=8.6 Hz, 2H, CH$_2$); 3.8–3.2 ppm (br, NH$_3^+$). MS (API-ES pos.): 228 [M+H]$^+$ (100).

12. 6-Amino-1,1'-biphenyl-2,4'-diol hydrochloride

Boric acid derivative used: 4-(tetrahydropyran-2-yloxy)phenylboric acid

Yield: 0.03 g (14% of the theoretical) MS (API-ES pos.): 202 [M+H]$^+$ (45).

13. 6'-Amino-2'-hydroxy-1,1'-biphenyl-4-carbaldehyde hydrochloride

Boric acid derivative used: 4-formylphenylboric acid

Yield: 0.07 g (30% of the theoretical) MS (API-ES pos.): 214 [M+H]$^+$ (80).

14. 3-Amino-2-(2-trifluoromethylphenyl)phenol hydrochloride

Boric acid derivative used: 2-trifluoromethylphenylboric acid

Yield: 0.045 g (15% of the theoretical) $^1$H-NMR (300 MHz, DMSO): δ=9.58 ppm (s, 1H, OH); 7.91 ppm (d, J=7.5 Hz, 1H, arom. H); 7.02 ppm (d, J=7.4 Hz, 1H, arom. H); 7.74 ppm (t, J=7.26 Hz, 1H, arom. H): 7.63 ppm (t, J=7.65 Hz, 1H, arom. H); 7.30 ppm (d, J=7.47 Hz, 1H, arom. H); 7.15 ppm (t, J=7.8 Hz, 1H, arom. H); 6.65–6.63 ppm (m, 2H, arom. H); 3.8–3.2 ppm (br, NH$_3^+$). MS (API-ES pos.): 254 [M+H]$^+$ (100).

15. 2',6-Diamino-1,1'-biphenyl-2-ol dihydrochloride

Boric acid derivative used: N-(tert.butoxycarbonyl)-2-amino-1-phenylboric acid

Yield: 0.120 g (44% of the theoretical) MS(API-ES pos.): 201 [M+H]$^+$ (50); 223 [M+Na] (35).

16. 3-Amino-2-(3-pyridinyl)phenol hydrochloride

Boric acid derivative used: 2-(pyridin-3-yl)-1,3,2-dioxaborolane

Yield: 0.088 g (39% of the theoretical) $^1$H-NMR (300 MHz, DMSO): δ=10.01 ppm (s, 1H, OH); 8.91–8.86 ppm (m, 2H, arom. H); 8.53 ppm (d, J=7.89 Hz, 1H, arom. H); 8.10 ppm (dd, J=5.76 and 7.8 Hz, 1H, arom. H); 7.18 ppm (t, J=8.1 Hz, 1H, arom. H); 6.68–6.65 ppm (m, 2H, arom. H); 4.1–3.5 ppm (br, NH$_3^+$). MS (API-ES pos.): 187 [M+H]$^+$ (100). MS (API-ES pos.): 187 [M+H]$^+$ (100).

17. 3-Amino-2-(4-pyridinyl)phenol hydrochloride

Boric acid derivative used: pyridin-4-ylboric acid

Yield: 0.130 g (58% of the theoretical) $^1$H-NMR (300 MHz, DMSO): δ=9.90 ppm (s, 1H, OH); 8.89 ppm (d, J=6.54 Hz, 2H, arom.$_{py}$ H); 8.05 ppm (d, 6.54 Hz, 2H, arom.$_{py}$ H); 7.07 ppm (t, 7.8 Hz, arom. H); 6.48–6.42 ppm (m, 2H, arom. H); 4.0–3.4 ppm (br, NH$_3^+$). MS (API-ES pos.): 187 [M+H]$^+$ (100).

Examples 18 to 34

Hair Colorants

Hair colorant solutions of the following composition were prepared:

| | |
|---|---|
| 1.25 mmol | of the substance of formula (I) as per Table 1 |
| 1.25 mmol | of the developer as per Table 1 |
| 10.0 g | of lauryl ether sulfate (28% aqueous solution) |
| 9.0 g | of ammonia (22% aqueous solution) |
| 7.8 g | of ethanol |
| 0.3 g | of ascorbic acid |
| 0.3 g | of disodium ethylenediaminetetraacetate hydrate |
| to 100.0 g | water, demineralized |

Just before use, 10 g of the above colorant solution was mixed with 10 g of a 6% hydrogen peroxide solution. The mixture was then applied to bleached hair. After an exposure time of 30 minutes at 40° C., the hair was rinsed with water, washed with a commercial shampoo and dried. Table 1 summarizes the resulting colorations.

TABLE 1

| | | Developer | | | | |
|---|---|---|---|---|---|---|
| | | I | II | III | IV | V |
| Example No. | Coupler of Formula (I) | 2,5-diamino-toluene sulfate | 2,5-diamino-phenylethanol sulfate | 4,5-diamino-1-(2'-hydroxy-ethyl)pyrazole sulfate | 4-aminophenol | 2,4,5,6-tetra-aminopyrimidine sulfate |
| 18 | as per Example 1 | violet | violet | strawberry red | weak orange-brown | blue-gray |

TABLE 1-continued

| Example No. | Coupler of Formula (I) | Developer | | | | |
|---|---|---|---|---|---|---|
| | | I 2,5-diamino-toluene sulfate | II 2,5-diamino-phenylethanol sulfate | III 4,5-diamino-1-(2'-hydroxy-ethyl)pyrazole sulfate | IV 4-aminophenol | V 2,4,5,6-tetra-aminopyrimidine sulfate |
| 19 | as per Example 2 | violet | violet | strawberry red | weak orange-brown | blue-gray |
| 20 | as per Example 3 | dark-violet | violet | strawberry red | orange | gray |
| 21 | as per Example 4 | violet | violet | strawberry red | weak orange-brown | gray |
| 22 | as per Example 5 | violet | violet | strawberry red | weak orange-brown | gray |
| 23 | as per Example 6 | brown | brown | strawberry red | weak orange-brown | weak green-brown |
| 24 | as per Example 7 | violet | violet | strawberry red | weak orange | gray |
| 25 | as per Example 8 | violetish brown | violetish brown | strawberry pink | weak orange | gray |
| 26 | as per Example 9 | brownish violet | brownish violet | strawberry red | orange | gray |
| 27 | as per Example 10 | violet-brown | violet-brown | red | weak orange | gray |
| 28 | as per Example 11 | violet | violet | red | weak orange | gray |
| 29 | as per Example 12 | red-violet | red-violet | red | orange | gray |
| 30 | as per Example 13 | violetish gray | violetish gray | strawberry red | weak orange-brown | gray |
| 31 | as per Example 14 | violetish gray | violetish gray | strawberry pink | weak orange | greenish gray |
| 32 | as per Example 15 | violet | violet | strawberry red | weak orange | gray |
| 33 | as per Example 16 | intense violet | intense violet | red | orange-brown | steel-gray |
| 34 | as per Example 17 | intense violet | intense violet | red | orange-brown | dull green |

Examples 35 to 58

Hair Colorants

Hair colorant solutions of the following composition were prepared:

| | | |
|---|---|---|
| X g | | of 3-aminophenol derivative of formula (I) (coupler K1 to K4 as per Table 4) |
| U g | | of developer E8 to E15 as per Table 2 |
| Y g | | of coupler K12 to K36 as per Table 4 |
| 10.0 g | | of lauryl ether sulfate (28% aqueous solution) |
| 9.0 g | | of ammonia (22% aqueous solution) |
| 7.8 g | | of ethanol |
| 0.3 g | | of ascorbic acid |
| 0.3 g | | of disodium ethylenediaminetetraacetate hydrate |
| to 100.0 g | | water, demineralized |

Just before use, 30 g of the above colorant solution was mixed with 30 g of a 6% aqueous hydrogen peroxide solution. The mixture was then applied to bleached hair. After an exposure time of 30 minutes at 40° C., the hair was rinsed with water, washed with a commercial shampoo and dried. Table 5 summarizes the resulting colorations.

TABLE 2

| Developers | |
|---|---|
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E13 | N,N-bis-(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| Direct Dyes | |
|---|---|
| D2 | 6-chloro-2-ethylamino-4-nitrophenol |
| D3 | 2-amino-6-chloro-4-nitrophenol |

TABLE 4

| Couplers | |
|---|---|
| K1 | 3-amino-2-(1,3-benzodioxol-5-yl)phenol |
| K2 | 3',6-diamino-1,1'-biphenyl-2-ol |
| K3 | 3-amino-2-(3-pyridinyl)phenol |
| K4 | 3-amino-2-(4-pyridinyl)phenol |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |

TABLE 4-continued

| | Couplers |
|---|---|
| K18 | N-(3-dimethylamino)phenylurea |
| K19 | 1,3-bis-(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxy-benzene hydroxide |
| K36 | 2-amino-5-methylphenol |

TABLE 5

Hair Colorants

| Dyes | 35 | 36 | 37 | 38 | 39 | 40 |
|---|---|---|---|---|---|---|
| | (Dye quantity in grams) | | | | | |
| K1 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

| Dyes | 41 | 42 | 43 | 44 | 45 | 46 |
|---|---|---|---|---|---|---|
| | (Dye quantity in grams) | | | | | |
| K2 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

| Dyes | 47 | 48 | 49 | 50 | 51 | 52 |
|---|---|---|---|---|---|---|
| | (Dye quantity in grams) | | | | | |
| K3 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

| Dyes | 53 | 54 | 55 | 56 | 57 | 58 |
|---|---|---|---|---|---|---|
| | (Dye quantity in grams) | | | | | |
| K4 | 0.10 | 0.12 | 0.05 | 0.07 | 0.10 | 0.12 |
| E8 | 0.30 | | | | | |
| E9 | | | | | 0.25 | 0.20 |
| E10 | | | | | | 0.10 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K25 | | | | | 0.10 | |
| K31 | 0.20 | | | 0.15 | 0.10 | 0.10 |
| K32 | | 0.20 | | 0.10 | | |
| K33 | | | 0.20 | | | |
| K36 | | | | | | 0.10 |
| Coloring result | blond | blond | blond | blond | blond | blond |

Examples 59 to 82

Hair Colorants

Hair colorant solutions of the following composition were prepared:

| | | |
|---|---|---|
| X g | | of 3-aminophenol derivative of formula (I) (coupler K1 to K4 as per Table 4) |
| U g | | of developer E8 to E15 as per Table 2 |
| Y g | | of coupler K11 to K36 as per Table 4 |
| Z g | | of direct dye D2 and/or D3 as per Table 3 |
| 10.0 g | | of lauryl ether sulfate (28% aqueous solution) |
| 9.0 g | | of ammonia (22% aqueous solution) |
| 7.8 g | | of ethanol |
| 0.3 g | | of ascorbic acid |
| 0.3 g | | of disodium ethylenediaminetetraacetate hydrate |
| to 100.0 g | | water, demineralized |

Just before use, 30 g of the above colorant cream was mixed with 30 g of a 6% aqueous hydrogen peroxide solution. The mixture was then applied to hair. After an exposure time of 30 minutes at 40° C., the hair was rinsed with water, washed with a commercial shampoo and dried. Table 6 summarizes the resulting colorations.

TABLE 6

Hair Colorants

| Dyes | \multicolumn{6}{c}{Example No.} | | | | | |
|---|---|---|---|---|---|---|
| | 59 | 60 | 61 | 62 | 63 | 64 |
| | \multicolumn{6}{c}{(Dye quantity in grams)} | | | | | |
| K1 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K19 | 0.10 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

| Dyes | \multicolumn{6}{c}{Example No.} | | | | | |
|---|---|---|---|---|---|---|
| | 65 | 66 | 67 | 68 | 69 | 70 |
| | \multicolumn{6}{c}{(Dye quantity in grams)} | | | | | |
| K2 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

| Dyes | \multicolumn{6}{c}{Example No.} | | | | | |
|---|---|---|---|---|---|---|
| | 71 | 72 | 73 | 74 | 75 | 76 |
| | \multicolumn{6}{c}{(Dye quantity in grams)} | | | | | |
| K3 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 0.05 |
| Coloring result | black | black | black | brown | brown | brown |

| Dyes | \multicolumn{6}{c}{Example No.} | | | | | |
|---|---|---|---|---|---|---|
| | 77 | 78 | 79 | 80 | 81 | 82 |
| | \multicolumn{6}{c}{(Dye quantity in grams)} | | | | | |
| K4 | 0.60 | 1.30 | 1.15 | 0.15 | 0.15 | 0.15 |
| E8 | 1.50 | | | | | |
| E11 | 0.10 | | | | | |
| E13 | | 1.60 | | | | 0.70 |
| E14 | | | | 0.10 | 0.10 | |
| E15 | | | 1.80 | 0.70 | 0.70 | |
| K12 | 0.50 | | | | | |
| K14 | 0.10 | | | | | |
| K18 | 0.05 | | | | | |
| K23 | | | 0.05 | 0.10 | 0.10 | 0.10 |
| K24 | 0.15 | | | | | |
| K31 | 0.90 | 1.10 | 1.10 | 0.40 | 0.40 | 0.40 |
| K34 | 0.10 | | | | | |
| D2 | | | | 0.10 | 0.10 | 0.10 |
| D3 | | | | 0.05 | 0.05 | 005 |
| Coloring result | black | black | black | brown | brown | brown |

Unless otherwise indicated, all percentages given in the present patent application are by weight.

What is claimed is:

1. A 3-Aminophenol derivative of formula (I), or a physiologically compatible, water-soluble salts thereof:

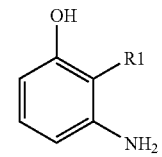

(I)

wherein R1 represents a group of formula (II) or (III)

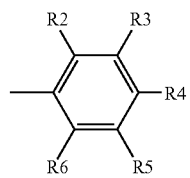

(II)

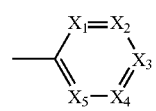

(III)

wherein
R2, R3, R4, R5 and R6 independently of each other denote hydrogen, a halogen atom, a cyano group, a hydroxyl group, a $C_1$–$C_4$-alkoxy group, a phenoxy group, a $C_2$–$C_4$-hydroxyalkoxy group, a $C_1$–$C_6$-alkyl group, a phenyl group, a $C_1$–$C_4$-alkyl thioether group, a mercapto group, a nitro group, an amino group, a $C_1$–$C_4$-alkylamino group, a hydroxy-($C_2$–$C_4$)-alkylamino group, a di($C_1$–$C_4$)-alkylamino group, a di[hydroxy-($C_2$–$C_4$)alkyl]amino group, a [dihydroxy-($C_3$–$C_4$)-alkyl]amino group, a [hydroxy-($C_2$–$C_4$)-alkyl]-$C_1$–$C_4$-alkylamino group, a trifluoromethyl group, a formyl group, an acetyl group, a trifluoroacetyl group, a trimethylsilyl group, a ($C_1$–$C_4$)-hydroxyalkyl group, a ($C_2$–$C_4$)-dihydroxyalkyl group, a ($C_1$–$C_4$)-aminoalkyl group or a ($C_1$–$C_4$)-cyanoalkyl group, or two adjacent R2 to R6 groups together with a remaining portion of the group of formula (II) form a heterocyclic or carbocyclic, substituted or unsubstituted ring; with the proviso that at least one of R2, R3, R4, R5 and R6 is other than hydrogen X1, X2, X3, X4 and X5 independently of each other denote nitrogen or a C—R7 group, C—R8 group, C—R9 group, C—R10 group or C—R11 group, provided that at least one and at the most three of the $X_1$ to $X_5$ groups denote nitrogen; and R7, R8, R9, R10 and R11 independently of each other denote hydrogen, a halogen atom, a cyano group, a $C_1$–$C_6$-alkyl group, a ($C_1$–$C_4$)-alkyl thioether group, a mercapto group, a nitro group, an amino group, a $C_1$–$C_4$-alkylamino group, a hydroxy-($C_2$–$C_4$)-alkylamino group, a di($C_1$–$C_4$)-alkylamino group, a di[hydroxy($C_2$–$C_4$)-alkyl]amino group, a [dihydroxy-($C_3$–$C_4$)-alkyl]amino group, a [hydroxy-($C_2$–$C_4$)-alkyl]-$C_1$–$C_4$-alkylamino group, a trifluoromethyl group, a formyl group, an acetyl group, a trifluoroacetyl group, a trimethylsilyl group, a carbamoyl group, a ($C_1$–$C_4$)-hydroxyalkyl group or a ($C_2$–$C_4$)-dihydroxyalkyl group.

2. A 3-Aminophenol derivative selected from the group consisting of 6-amino-4'-methyl-[1,1'-biphenyl]-2-ol, 6-amino-3'-methyl-[1,1'-biphenyl]-2-ol, 6-amino-2'-methyl-[1,1'-biphenyl]-2-ol, 6-amino-2',3'-dimethyl-[1,1'-biphenyl]-2-ol, 6-amino-2',4'-dimethyl-[1,1'-biphenyl]-2-ol, 6-amino-2',5'-dimethyl-[1,1'-biphenyl]-2-ol, 6-amino-2',6'-dimethyl-[1,1'-biphenyl]-2-ol, 6-amino-3',4'-dimethyl-[1,1'-biphenyl]-2-ol, 6-amino-3',5'-dimethyl-[1,1'-biphenyl]-2-ol, 6-amino-3',6'-dimethyl-[1,1'-biphenyl]-2-ol, 6-amino-2',4',5'-trimethyl-[1,1'-biphenyl]-2-ol, 6-amino-2',4',6'-trimethyl-[1,1'-biphenyl]-2-ol, 6-amino-2',3',4'-trimethyl-[1,1'-biphenyl]-2-ol, 6-amino-2',3',5'-trimethyl-[1,1'-biphenyl]-2-ol, 6-amino-2',3',6'-trimethyl-[1,1'-biphenyl]-2-ol, 6-amino-4'-chloro-[1,1'-biphenyl]-2-ol, 6-amino-3'-chloro-[1,1'-biphenyl]-2-ol, 6-amino-2'-chloro-[1,1'-biphenyl]-2-ol, 6-amino-4'-fluoro-[1,1'-biphenyl]-2-ol, 6-amino-3'-fluoro-[1,1'-biphenyl]-2-ol, 6-amino-2'-fluoro-[1,1'-biphenyl]-2-ol, 6-amino-4'-bromo-[1,1'-biphenyl]-2-ol, 6-amino-3'-bromo-[1,1'-biphenyl]-2-ol, 6-amino-2'-bromo-[1,1'-biphenyl]-2-ol, 6-amino-3',5'-dicloro-[1,1'-biphenyl]-2-ol, 6-amino-3',5'-difluoro-[1,1'-biphenyl]-2-ol, 6-amino-3'-bromo-5'-methyl-[1,1'-biphenyl]-2-ol, 6-amino-4'-(trifluoromethyl)-[1,1'-biphenyl]-2-ol, 6-amino-3'-(trifluoromethyl)-[1,1'-biphenyl]-2-ol, 6-amino-2'-(trifluoromethyl)-[1,1'-biphenyl]-2-ol, 6-amino-4'-nitro-[1,1'-biphenyl]-2-ol, 6-amino-3'-nitro-[1,1'-biphenyl]-2-ol, 6-amino-2'-nitro-[1,1'-biphenyl]-2-ol, 6-amino-5'-methyl-3'-nitro-[1,1'-biphenyl]-2-ol, 6-amino-4'-methyl-3'-nitro-[1,1'-biphenyl]-2-ol, 6-amino-2'-methyl-3'-nitro-[1,1'-biphenyl]-2-ol, 6-amino-2'-nitro-4'-(trifluoromethyl)-[1,1'-biphenyl]-2-ol, 6-amino-3'-nitro-5'-(trifluoromethyl)-[1,1'-biphenyl]-2-ol, 6-amino-3'-nitro-4'-(trifluoromethyl)-[1,1'-biphenyl]-2-ol, 6-amino-3'-nitro-2'-(trifluoromethyl)-[1,1'-biphenyl]-2-ol, 6'-amino-2'-hydroxy-[1,1'-biphenyl]-4-carbonitrile, 6'-amino-2'-hydroxy-[1,1'-biphenyl]-3-carbonitrile, 6-amino-4'-methoxy-[1,1'-biphenyl]-2-ol, 6-amino-3'-methoxy-[1,1'-biphenyl]-2-ol, 6-amino-2'-methoxy-[1,1'-biphenyl]-2-ol, 6-amino-4'-ethoxy-[1,1'-biphenyl]-2-ol, 6-amino-3'-ethoxy-[1,1'-biphenyl]-2-ol, 6-amino-2'-ethoxy-[1,1'-biphenyl]-2-ol, 6-amino-3',4'-dimethoxy-[1,1'-biphenyl]-2-ol, 6-amino-3',5'-dimethoxy-[1,1'-biphenyl]-2-ol, 6-amino-2',3'-dimethoxy-[1,1'-biphenyl]-2-ol, 6-amino-2',4'-dimethoxy-[1,1'-biphenyl]-2-ol, 6-amino-2 ',5'-dimethoxy-[1,1'-biphenyl]-2-ol, 3-amino-2-(1,3-benzo-dioxol-5-yl)phenol, 6-amino-4'-methoxy-3'-methyl-[1,1'-biphenyl]-2-ol, 6-amino-4'-methoxy-2'-nitro-[1,1'-biphenyl]-2-ol, 6-amino-4'-methoxy-3'-nitro-[1,1'-biphenyl]-2-ol, 6-amino-4'-phenoxy-[1,1'-biphenyl]-2-ol, 6-amino-4'-methylthio-[1,1'-biphenyl]-2-ol, 6-amino-3'-methyl-thio-[1,1'-biphenyl]-2-ol, 6-amino-2'-methyl-thio-[1,1'-biphenyl]-2-ol, 6-amino-[1,1'-biphenyl]-2,4'-diol, 6-amino-[1,1'-biphenyl]-2,3'-diol, 6-amino-[1,1'-biphenyl]-2,2'-diol, 2,2'3'-trihydroxy-6-amino-[1,1'-biphenyl], 2,2'4'-trihydroxy-6-amino-[1'-biphenyl], 2,2'5'-trihydroxy-6-amino-[1,1'-biphenyl], 2,2'6'-trihydroxy-6-amino-[1,1'-biphenyl], 2,3',4'-trihydroxy-6-amino-[1,1'-biphenyl], 2,3',5'-trihydroxy-6-amino-[1,1'-biphenyl], 6-amino-2'-methyl-[1,1'-biphenyl]-2,4'-diol, 2',6-diamino-[1,1'-biphenyl]-2-ol, 3',6-diamino-[1,1'-biphenyl]-2-ol, 4',6-diamino-[1,1'-biphenyl]-2-ol, 4',6-diamino-[1,1'-biphenyl]-2,2'-diol, 3',6-diamino-[1,1'-biphenyl]-2,2'-diol, 3',6-diamino-[1,1'-biphenyl]-2,4'-diol, 3',6-diamino-[1,1'-biphenyl]-2,5'-diol, 3',6-diamino-[1,1'-biphenyl]-2,6'-diol, 2',3',6-triamino-[1,1'-biphenyl]-2-ol, 2',4',6-triamino-[1,1'-biphenyl]-2-ol, 2',5',6-triamino-[1,1'-biphenyl]-2-ol, 2',6,6'-triamino-[1,1'-biphenyl]-2-ol, 3',4',6-triamino-[1,1'-biphenyl]-2-ol, 3',5',6-triamino-[1,1'-biphenyl]-2-ol, 1-(6'-amino-2'-hydroxy-1,1'-biphenyl-4-yl)ethanone, 6-amino-1,1',3',1''-terphenyl-2-ol, 6-amino-1,1',4',1''-terphenyl-2-ol, 6-amino-4'-(amino-methyl)-1,1'-biphenyl-2-ol, 6-amino-3'-(aminomethyl)-1,1'-biphenyl-2-ol, 6-amino-2'-(aminomethyl)-1,1'-biphenyl-2-ol, (6'-amino-2'-hydroxy-1,1'-biphenyl-4-yl)acetonitrile, (6'-amino-2'-hydroxy-1,1'-biphenyl-3-yl)acetonitrile, (6'-amino-2'-hydroxy-1,1'-biphenyl-2-yl)acetonitrile, 6'-amino-2'-hydroxy-1,1'-biphenyl-2-carbaldehyde, 6'-amino-2'-hydroxy-1,1'-biphenyl-3-carbaldehyde, 6'-amino-2'-hydroxy-1,1'-biphenyl-4-carbaldehyde, 3-amino-2-(1-naphthyl)phenol, 3-amino-2-(2-naphthyl)phenol, 3-amino-2-(2,3-dihydrobenzo[1,4]dioxin-6-yl)phenol, 3-amino-2-(2,3-dihydrobenzo[1,4]-dioxin-5-yl)phenol, 3-amino-2-(2,3-dihydrobenzofuran-5-yl)phenol, 3-amino-2-(2,3-dihydrobenzofuran-4-yl)phenol, 3-amino-2-(4-pyridinyl)phenol, 3-amino-2-(3-pyridinyl)-phenol, 3-amino-2-(2-pyridinyl)-phenol, 3-amino-2-(3-methyl-2-pyridinyl)-phenol, 3-amino-2-(4-methyl-2-pyridinyl)-phenol, 3-amino-2-(5-methyl-2-pyridinyl)-phenol, 3-amino-2-(6-methyl-2-pyridinyl)-phenol, 3-amino-2-(3-chloro-2-pyridinyl)-phenol, 3-amino-2-(4-chloro-2-pyridinyl)-phenol, 3-amino-2-(5-chloro-2-pyridinyl)-phenol, 3-amino-2-(6-chloro-2-pyridinyl)-phenol, 3-amino-2-(3-fluoro-2-pyridinyl)-phenol, 3-amino-2-(4-fluoro-2-pyridinyl)-phenol, 3-amino-2-(5-fluoro-2-pyridinyl)-phenol, 3-amino-2-(6-fluoro-2-pyridinyl)-phenol, 3-amino-2-(3-trifluoromethyl)-2-pyridinyl)-phenol, 3-amino-2-(4-trifluoromethyl-2-pyridinyl)-phenol, 3-amino-2-(5-trifluoromethyl-2-pyridinyl)-phenol, 3-amino-2-(6-trifluoromethyl-2-pyridinyl)-phenol, 3-amino-2-(3-nitro-2-pyridinyl)-phenol, 3-amino-2-(4-nitro-2-pyridinyl)-phenol, 3-amino-2-(5-nitro-2-pyridinyl)phenol, 3-amino-2-(6-nitro-2-pyridinyl)-phenol, 3-amino-2-(2-methyl-3-pyridinyl)phenol, 3-amino-2-(4-methyl-3-pyridinyl)-phenol, 3-amino-2-(5-methyl-3-pyridinyl)-phenol, 3-amino-2-(6-methyl-3-pyridinyl)-phenol, 3-amino-2-(2-chloro-3-pyridinyl)-phenol, 3-amino-2-(4-chloro-3-pyridinyl)-phenol, 3-amino-2-(5-chloro-3-pyridinyl)-phenol, 3-amino-2-(6-chloro-3-pyridinyl)-phenol, 3-amino-2-(2-bromo-3-pyridinyl)-phenol, 3-amino-2-(4-bromo-3-pyridinyl)-phenol, 3-amino-2-(5-bromo-3-pyridinyl)-phenol, 3-amino-2-(6-bromo-3-pyridinyl)phenol, 3-amino-2-(2-nitro-3-pyridinyl)-phenol, 3-amino-2-(4-nitro-3-pyridinyl)phenol, 3-amino-2-(5-nitro-3-pyridinyl)-phenol, 3-amino-2-(6-nitro-3-pyridinyl)phenol, 3-amino-2-(5-pyrimidinyl)phenol and 3-amino-2-(4-pyrimidinyl)phenol or a physiologically compatible, water-soluble salts thereof.

3. The 3-Aminophenol derivative according to claim 1, wherein R1 denotes the group of the formula (II) with R2 or R6 denoting hydrogen, or R1 denotes the group of the formula (III) with $X_1$ or $X_5$ denoting C—R7 or C—R11, and R7 or R11 denoting hydrogen.

4. The 3-Aminophenol derivative according to claim 1, wherein the derivative is selected from the group consisting of 6-amino-3'-methoxy-[1,1'-biphenyl]2-ol, 6-amino-[1,1'-biphenel]-2,4'-diol, 3-amino-2-(2,3-dihydrobenzo[1,4]dioxin-6-yl)-phenol, 3-amino-2-(2,3-dihydrobenzofuran-5-yl)-phenol, 3-amino-2-(3-pyridinyl)-phenol, 3-amino-2-(4-pyridinyl)-phenol and 3-amino-2-(5-pyrimidinyl)-phenol, or a physiologically compatible, water-soluble salt thereof.

5. Agent for coloring keratin fibers, said agent containing at least one coupler and at least one developer, wherein said at least one coupler comprises at least one 3-aminophenol derivative of the formula (I) according to claim 1.

6. Agent according to claim 5, containing the at least one 3-aminophenol derivative of the formula (I) in an amount from 0.005 to 20 weight percent.

7. Agent according to claim 5, wherein the at least one developer is selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(2-thienyl)-benzene, 1,4-diamino-2-(3-thienyl) benzene, 1,4-diamino-2-(pyridin-3-yl)benzene, 2,5-diaminobiphenyl, 4-diamino-2-methoxymethylbenzene, 1,4-diamino-2-aminomethylbenzene, 1,4-diamino-2-hydroxymethylbenzene, 1,4-diamino-2-(2-hydroxyethoxy)-benzene, 2-[2-(acetylamino)ethoxy]-1,4-diaminobenzene, 4-phenylaminoaniline, 1,4-dimethylaminoaniline, 4-diethylaminoaniline, 4-dipropylaminoaniline, 4-[ethyl-(2-hydroxyl)amino]-aniline, 4-[di(2-hydroxyethyl)amino]-aniline, 4-[di(2-hydroxyethyl)amino]-2-methyl-aniline, 4-[(2-methoxyethyl)amino]-aniline, 4-[(3-hydroxypropyl)amino]aniline, 4-[(2,3-dihydroxypropyl)amino]-aniline, 1,4-diamino-2-(1-hydroxyethyl)benzene, 1,4-diamino-2-(2-hydroxyethyl)benzene, 1,4-diamino-2-(1-methylethyl)benzene, 1,3-bis-[(4-aminophenyl)-( 2-hydroxyethyl)-amino]-2-propanol, 1,4-bis-[(4-amino-phenyl)amino]butane, 1,8-bis-[2,5-diaminophenoxy]-3,6-dioxaoctane, 4-aminophenol, 4-amino-3-methylphenol, 4-amino-3-(hydroxymethyl)-phenol, 4-amino-3-fluorophenol, 4-methylaminophenol, 4-amino-2-(aminomethyl)phenol, 4-amino-2-(hydroxymethyl)-phenol, 4-amino-2-fluorophenol, 4-amino-2-[(2-hydroxyethyl)amino]-methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

8. Agent according to one claim 5, whwrein said at least one coupler includes at least one compound selected from the group consisting of N-(3-dimethylaminophenyl)urea, 2,6-diaminopyridine, 2-amino-4-[(2-hydroxyethyl)amino] anisole, 2,4-diamino-1-fluoro-5-methylbenzene, 2,4-diamino-1-methoxy-5-methylbenzene, 2,4-diamino-1-ethoxy-5-methylbenzene, 2,4-di-amino-1-(2-hydroxyethoxy)-5-methylbenzene, 2,4-di[(2-hydroxyethyl)amino]-1,5-dimethoxy-benzene, 2,3-diamino-6-methoxy-pyridine, 3-amino-6-methoxy-2-(methylamino)pyridine, 2,6-di-amino- 3,5-dimethoxypyridine, 3,5-diamino-2,6-dimethoxypyridine, 1,3-diaminobenzene, 2,4-diamino-1-(2-hydroxyethoxy)-benzene, 1,3-diamino-4-(2,3-dihydroxypropoxy)-benzene, 1,3-diamino-4-(3-hydroxypropoxy)-benzene, 1,3-diamino-4-(2-methoxyethoxy)-benzene, 2,4-diamino-1,5-di(2-hydroxyethoxy)-benzene, 1-(2-amino-ethoxy)-2,4-diaminobenzene, 2-amino-1-(2-hydroxyethoxy)-4-methylaminobenzene, 2,4-diaminophenoxyacetic acid, 3-[di (2-hydroxyethyl)-amino]aniline, 4-amino-2-di-[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di-(2,4-diamino-phenoxy)-propane, 1,3-di(2,4-diamino-phenoxy)methane, 1,3-diamino-2,4-dimethoxy-benzene, 2,6-bis-(2-hydroxyethyl)-aminotoluene, 4-hydroxyindole, 3-dimethylamino-phenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]-acetamide, 5-[(2-hydroxyethyl)amino]-4-methoxy-2-methylphenol, 5-[(2-hydroxyethyl)amino]-2-methylphenol-3-[(2-hydroxyethyl)amino]phenol, 3-[(2-methoxyethyl)-amino]phenol, 5-amino-2-ethylphenol, 5-amino-2-methoxyphenol, 2-(4-amino-2-hydroxyphenoxy)-ethanol, 5-[(3-hydroxypropyl) amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl) amino]-1,3-benzodioxole, 6-bromo-1-hydroxy-3,4-methylene-dioxybenzene, 3,4-diaminobenzoic acid, 3,4-dihydro-6-hydroxy-1,4-(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

9. Agent according to one of claim 5, containing said at least one developer and said at least one coupler each in an amount of 0.005 to 20 weight percent, based on a total amount of the agent.

10. Agent according to claim 5, further comprising at least one direct dye.

11. Agent according to claim 5, having pH from 6.5 to 11.5.

12. Ready-for-use agent for oxidative dyeing of keratin fibers, said agent containing in a medium suitable for dyeing at least one developer and at least one coupler as well as at least one oxidant, wherein said at least one coupler comprises at least one 3-aminophenol derivative of the formula (I) according to claim 1.

13. Agent according to claim 5, consisting of hair colorant.

14. Method for oxidative dyeing of hair, particularly human hair, wherein before use, the hair colorant according to claim 13 is mixed with an oxidant, applied to the hair and allowed to act on the hair at a temperature from 15 to 50° C. for 10 to 45 minutes, after which the hair is rinsed with water, optionally washed with a shampoo and then dried.

* * * * *